United States Patent [19]

Schonenberger et al.

[11] Patent Number: 4,745,233
[45] Date of Patent: May 17, 1988

[54] DERIVATIVES OF 1,1,2,2-TETRAMETHYL-1,2-BIS-(2-FLUORO-4-HYDROXYPHENYL)-ETHANE

[75] Inventors: Helmut Schonenberger, Pentling; Rolf W. Hartmann, Abbach; Martin Schneider, Regensburg; Walter Schwarz, Pentling; Jurgen Engel, Alzenau, all of Fed. Rep. of Germany

[73] Assignee: Asta-Werke Aktiengesellschaft, Bielefeld, Fed. Rep. of Germany

[21] Appl. No.: 871,892

[22] Filed: Jun. 9, 1986

[30] Foreign Application Priority Data

Jun. 8, 1985 [DE] Fed. Rep. of Germany ....... 3520622

[51] Int. Cl.$^4$ ................ C07C 39/14; C07C 125/04; C07C 125/06
[52] U.S. Cl. .................................. 568/729; 514/483; 514/490; 514/548; 514/549; 514/550; 558/62; 560/133; 560/138; 568/726
[58] Field of Search ............... 568/726, 729; 558/62; 514/651, 679, 483, 490, 548, 549, 550; 560/133, 138

[56] References Cited

U.S. PATENT DOCUMENTS 4,427,697 1/1984 Chan ................................ 568/729
4,467,121 8/1984 Marks et al. ..................... 568/726

FOREIGN PATENT DOCUMENTS 2021588 5/1979 United Kingdom ............ 568/729

Primary Examiner—Werren B. Lone
Attorney, Agent, or Firm—Cushman, Darby & Cushman

[57] ABSTRACT

Antitumor compounds corresponding to the following formula:

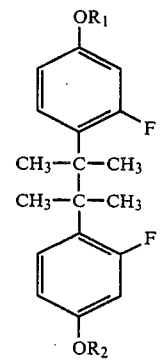

I in which the substituents $R_1$ and $R_2$ may be the same or different and represent hydrogen, an aminocarbonyl group, a $C_1$-$C_6$ alkylaminocarbonyl group, a di-$C_1$-$C_6$-alkylaminocarbonyl group, the group $PO(OH)_2$, a $C_2$-$C_8$ alkanoyl group, a $C_2$-$C_8$ halogen alkanoyl group or a $C_3$-$C_8$ alkenoyl group, a process for their preparation, and their use in treating oestrogen-receptor-positive-tumors as well as the prostate carcinoma.

10 Claims, No Drawings

DERIVATIVES OF 1,1,2,2-TETRAMETHYL-1,2-BIS-(2-FLUORO-4-HYDROXYPHENYL)-ETHANE

BACKGROUND OF THE INVENTION

The true antioestrogen, 1,1,2,2-tetramethyl-1,2-bis-(4-hydroxyphenyl)-ethane (R. W. Hartmann, *Eur. J. Cancer Clin. Oncol.* 1983, 19 959), shows considerable affinity for the oestrogen receptor (relative binding affinity=3.6). This compound shows for example a strong effect as antioestrogen by inhibiting the oestrone- or oestradiol-stimulated uterus growth of juvenile mice and inhibits the growth of the mammary carcinoma induced in rats (Sprague Dawley rats) by 7,12-dimethylbenzanthracene (DMBA), an experimental tumor which is very similar in its behavior to the human mammary carcinoma (MC).

SUMMARY OF THE INVENTION

The compounds of the invention correspond to the following formula:

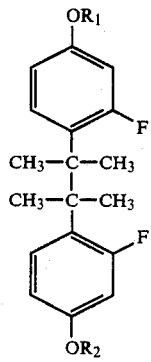

I in which the substituents $R_1$ and $R_2$ may be the same or different and represent hydrogen, an aminocarbonyl group, a $C_1$–$C_6$ alkylaminocarbonyl group, a di-$C_1$–$C_6$-alkylaminocarbonyl group, the group $PO(OH))_2$, a $C_2$–$C_8$ alkanoyl group, a $C_2$–$C_8$ halogen alkanoyl group or a $C_3$–$C_8$ alkenoyl group, a process for their preparation and their use in treating oestrogen-receptor-positive tumors.

Examples of $C_1$–$C_6$ alkylaminocarbonyl are methylaminocarbonyl, ethylaminocarbonyl, propylaminocarbonyl, isopropylaminocarbonyl, butylaminocarbonyl, hexylaminocarbonyl. Examples of di-$C_1$–$C_6$-alkylamino carbonyl groups are dimethylaminocarbonyl, diethylamino-carbonyl, methyl ethyl aminocarbonyl, diisopropylaminocarbonyl, dipropylaminocarbonyl, dibutylaminocarbonyl. Examples of $C_2$–$C_8$-alkanoyl groups are acetyl, propionyl, butyryl, valeroyl, hexanoyl, octanoyl. Examples of $C_2$–$C_8$ halogen alkanoyl groups are chloroacetyl, dichloroacetyl, trichloroactyl, bromoacetyl, iodoacetyl, alpha-chloropropionyl, beta-chloropropionyl, omega-chlorobutyryl, omega chlorohexanoyl. Examples of $C_3$–$C_8$ alkenyloyl groups are acroyl, methacroyl, ethacroyl, crotonoyl.

The compounds are prepared by a process comprising in a compound corresponding to the following formula:

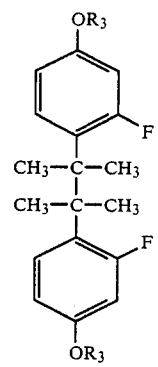

II in which $R_3$ is a $C_1$–$C_4$ alkyl group eliminating these two alkyl groups and optionally acylating the resulting compound of formula I, in which the two substituents $R_1$ and $R_2$ are hydrogen, by the substituents $R_1$ and $R_2$ other than hydrogen, and optionally converting $C_3$–$C_8$ halogen alkanoyl groups present in the resulting compounds into $C_3$–$C_8$ alkenoyl groups by elimination of hydrogen halide.

The compounds according to the invention surprisingly show a considerably increased affinity for the oestrogen receptor (relative binding affinity of the compound according to Example 1=11) and show a considerably greater effect on the DMBA-tumor than the known compound.

The compounds according to the invention are antioestrogens and show a strong oestrogen-antagonistic effect, for example in the uterus weight test in juvenile mice.

The compounds according to the invention show strong antitumor activity on oestrogen-receptor-positive tumors because they become concentrated in hormone-dependent tumors.

The compounds according to the invention are particularly suitable for the treatment of hormone-dependent tumors, particularly the hormone-dependent mammary carcinoma. However, they are also suitable, for example, for the treatment of the prostate carcinoma because they reduce the weight of target organs (such as for example the seminal vesicle) in mice and considerably reduce the testosterone level. Another very important factor is that the antioestrogenic compounds according to the invention show only minimal oestrogenic effects. With compounds corresponding to formula I, in which $R_1$ and $R_2$ are not hydrogen atoms, the phase of metabolization to the water-soluble metabolite does not occur. Accordingly, the half-life of these compounds is increased so that their antitumor effect is long-lasting. The compounds of the type in question are particularly suitable for peroral administration or for application in slow-release form. As a water-soluble compound, the compound of formula I in which $R_1$ and $R_2$ represent the group —$PO(OH)_2$ is particularly suitable for intravenous application. The substituents $R_1$ and $R_2$ are preferably the same. If one or both substituents $R_1$ and $R_2$ contain alkyl groups or represent alkenoyl groups, halogen alkanoyl groups or alkenoyl groups, these groups may be linear or branched. If the substituents $R_1$ and/or $R_2$ are $C_2$–$C_8$ alkanoyl groups, these groups preferably consist of from 1 to 4 carbon atoms. The groups in question are in particular acetyl groups. If these alkanoyl groups contains halogen atoms, the halogen atoms may be situated at one or several carbon atoms; the halogen atoms (particularly chlorine and bromine) may number from 1 to 3. Examples of halogen alkanoyl groups are $CHCl_2$—CO, $CH_2Cl$—CO, $CCl_3$—CO—, $CH_2Cl$—$CH_2$—CO, $CH_2Br$—$CH_2$—CO, $CHCl_2$—$CH_2$—CO—, $CHBr_2$—$CH_2CO$—, $CH_2Cl$—CHCl—CO, $CH_2Br$—CHBr—CO, $CHCl_2$—CHCl—CO—, $CH_2Br$—CHBr—CO—. If $R_1$ and/or $R_2$ represent $C_3$-$C_8$ alkenoyl groups, these groups consist in particular of from 3 to 6 carbon atoms. In this case, the group in question is preferably the $CH_2$=CH—CO group (acroyl group).

The process according to the invention is carried out at a temperature in the range of from $-70°$ C. to $+250°$ C.

The $C_1$-$C_4$ alkyl groups (ether groups) are eliminated, for example, in the absence of a solvent or in the presence of an inert solvent, such as boron tribromide, boron trifluoride, aluminium chloride, silicon tetrachloride, aluminium tribromide, sodium ethylthiolate, $(CH_3)_3SiCl+NaI$, at temperatures of from $-70°$ C. to $200°$ C. Suitable solvents for elimination of the ether groups are, for example, aliphatic halogenated hydrocarbons, such as for example methylene chloride, aromatic hydrocarbons, such a benzene, toluene, xylene, halogenated aromatic hydrocarbons, such as chlorobenzene, dichlorobenzenes, dimethylformamide, acetonitrile, nitrobenzene, carbon disulfide and dioxane.

Elimination of the ether groups may also be carried out using concentrated hydroiodic acid, hydrobromic acid (particularly in mixtures with acetic acid and acetic acid anhydride), pyridine hydrochloride, sulfuric acid, trifluoroacetic acid, phosphoric acid, chloro-, methyl-, p-toluene sulfonic acid, methylmagnesium iodide in the presence or absence of solvents at temperatures of from $20°$ C. to $250°$ C. Suitable solvents for this method of elimination are, for example, aliphatic ethers containing $C_1$-$C_6$ alkyl groups, toluene and benzene.

The acylation step of the process according to the invention is carried out with an acid corresponding to the formula R—OH, where R is an aminocarbonyl group, a $C_1$-$C_6$ alkylaminocarbonyl group, a di-$C_1$-$C_6$-alkylaminocarbonyl group, the group $PO(OH)_2$, a $C_2$-$C_8$ alkanoyl group or a $C_2$-$C_8$ halogen alkanoyl group, the acid in question preferably being activated. Where an activated acid is used for the acylation, it is preferably selected from compounds corresponding to the formula R-X, in which R is as defined above and X represents a halogen atom, a group of the formula —OR′, —SR′ or a group of the formula —OSO$_3$H or —OCO—R″ where R′ is a $C_1$-$C_6$ alkyl group or, in the case of —OR′ or —SR′, also a phenyl group; a phenyl group substituted by one or more nitro groups, $C_1$-$C_4$ alkoxy groups, $C_1$-$C_4$ alkyl groups or halogen atoms (chlorine, fluorine, bromine); a cyanomethyl group; or a carboxymethyl group, and where R″ is a straight-chain or branched $C_1$-$C_7$ alkyl group, a $C_1$-$C_7$ halogen alkyl group, a $C_1$-$C_6$ alkoxy group, a phenoxy group or a benzyloxy group; R may also represent the group COCl, POCl$_2$ or the cyano group where X is halogen and, in the case of COCl, amination is carried out by reaction in the usual way with $NH_3$, a $C_1$-$C_6$ alkylamine or a di-$C_1$-$C_6$-alkylamine and in the case of POCl$_2$ or the cyano group, hydrolysis is carried out with a mineral acid (sulfuric acid or hydrochloric acid or a mixture of both acids). This hydrolysis reaction is carried out, for example, in aqueous medium at temperatures of from $50°$ C. to $80°$ C.

Where X is a halogen atom, the halogen atom in question is preferably chlorine, bromine or iodine; where R′ or R″ is an alkyl group, a halogen alkyl group or an alkoxy group, these groups are preferably of low molecular weight and consist of from 1 to 4 carbon atoms.

The acylation step is carried out, for example, in a standard solvent or suspending agent, such as water, optionally with addition of a solution promoter (for example lower aliphatic alcohols, e.g. ethanol or isopropanol, lower aliphatic ketones, e.g. acetone, dimethylformamide) or inert media. Suitable solvents or suspending agents are, for example, low molecular weight aliphatic ethers (for example 4 to 10 carbon atoms, e.g. diethyl ether), low molecular weight aliphatic ketones (for example 3 to 6 carbon atoms, e.g. acetone, methyl ethyl ketone); saturated cyclic ethers, such as tetrahydrofuran, dioxane, low molecular weight saturated chlorinated and fluorinated hydrocarbons containing from 1 to 5 carbon atoms, the individual carbon atoms optionally being substituted once or several times (2 to 3 times) by chlorine and/or fluorine, such as chloroform, methylene chloride, dichlorodifluoroethane, aromatic hydrocarbons optionally substituted by chlorine or bromine, such as benzene, toluene, xylene, chlorobenzene, dimethylformamide, dimethylsulfoxide, tetramethylurea, pyridine, N-methyl-pyrrolidone. Mixtures of these solvents may of course also be used.

The acylation is carried out, for example, at temperatures of from $0°$ to $200°$ C. and preferably at temperatures of from $15°$ to $150°$ C.

In many cases, particularly where X is a halogen atom or represents the group —OCOR″, the presence of an acid-binding agent, such as alkali hydroxide, e.g. sodium hydroxide, potassium hydroxide, alkali carbonates, e.g. sodium carbonate, alkali hydrogen carbonates, e.g. sodium bicarbonate, alkali acetates, e.g. sodium acetate, alkaline earth carbonates, e.g. calcium carbonate, trialkylamines, e.g. triethyl amine, dialkylamines, e.g. diethylamine, pyridine and the like is advisable. The acid-binding agent may also be used simultaneously as solvent either on its own or in admixtures with other standard media (for example pyridine).

The acylation may also be carried out by initially preparing an alkali compound of the compound to be reacted by reacting it with an alkali metal, alkali hydride or alkali amine (particularly sodium or sodium compounds) in an inert solvent, such as dioxane, dimethylformamide, benzene or toluene at temperatures of from $0°$ to $150°$ C. and, for example, subsequently adding the acylating agent (compound R—X, R=halogen).

Where the free acid R—OH is used, it has to be activated by the presence of condensation agents, such as dicyclohexylcarbodiimide, tetraethylprophosphite, 5-(3′-sulfonephenyl)-ethylisooxazole, sulfurous acid-bisalkylamide (for example $SO[N(CH_3)_2]_2$, N,N′-carbonyl diimidazole and so on (Organic Reactions, Volume 12, 1962, pages 205 and 239).

Compounds corresponding to formula I, in which one or both substituents $R_1$ and $R_2$ represent a $C_3$-$C_8$ alkenoyl group, may also be obtained from corresponding compounds I in which one or both of these substituents is/are a $C_3$-$C_8$ alkanoyl group containing a chlorine or bromine atom (preferably in the $\beta$-position) by eliminating the halogen atom with a base, for example a tertiary amine, such as triethylamine, tripropylamine, N-methylpyrrolidone and pyridine) with formation of a double bond (for example in the α-β position). This reaction takes place, for example, at temperatures of from 30° to 150° C. in an inert solvent (aromatic hydrocarbons, such as toluene, xylene, and chlorobenzene, or halogenated hydrocarbons, such a methylene chloride or chloroform).

The acyl groups in the compounds of formula I may be split off again by solvolysis to give the corresponding free hydroxy compounds of formula I. This solvolytic elimination is carried out, for example, by hydrolysis with dilute acids, or by means of basic substances (potash, soda, aqueous alkali solutions, alcoholic alkali solutions, $NH_3$) at temperatures of from 10° to 150° C. and more especially at temperatures of from 20° to 100° C.

Selective elimination is also possible by splitting off only one acyl group ($R_1$ or $R_2$). Selective elimination such as this may be obtained, for example, by reaction of a corresponding diester with alkali hydroxide in a molar ratio of 1:1 at temperatures below 50° C.

The starting compounds of formula II are prepared, for example, by reductive coupling a compound corresponding to the following formula:

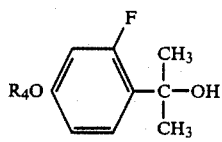

III in which $R_4$ is a $C_1$-$C_6$ alkyl group, particularly the methyl group, in the presence of titanium trichloride and a complex alkali hydride or the corresponding chloride (in which case the hydroxy group in formula III is replaced by Cl) with ethylmagnesium bromide in the presence of cobalt dichloride.

This method of preparing the starting compound II is carried out in a solvent or suspending agent, such as saturated low molecular weight aliphatic or cycloalipathic ethers (dimethoxyethane, diethylether, dioxane, tetrahydrofuran) at temperatures of from 30° to 100° C. The reaction time is for example between 6 and 18 hours. The reductive coupling using $TiCl_3$ is carried out, for example, by initially preparing the titanium (II)-containing coupling reagent from titanium trichloride and a complex alkali hydride (for example lithium aluminium hydride) in a suspending agent using the method described by McMurry and Silvestri in J. Org. Chem., Volume 40, No. 18, 1975 for example pages 2687-2688. Suitable suspending agents are saturated, low molecular weight aliphatic or cycloaliphatic ethers, such as dimethoxyethane, diethylether, dioxane, tetrahydrofuran. Suitable complex alkali hydrides are, for example, alkali borohydrides or alkali aluminium hydrides. Suitable alkali atoms are, for example, lithium and sodium.

The alcohol corresponding to formula III is then added to the suspension of the titanium (II)-containing coupling reagent in a solvent, particularly an ether of the type mentioned above, and the mixture thus obtained is heated for a prolonged period to a temperature of 93° C.

Where ethylmagnesium bromide is used, the chloride obtained from the alcohol III is for example added dropwise to a solution of ethylmagnesium bromide in a saturated, low molecular weight, aliphatic or cycloalipathic ether (diethylether, dioxane, tetrahydrofuran) to which anhydrous $COCl_2$ has been added. This reaction is preferably carried out at room temperature (cf. J. Med. Chem., 1981, Volume 24, pages 1192-1197).

The compounds according to the invention show a favorable tumor-inhibiting effect on DMBA-induced mammary carcinomas in Sprague-Dawley (SD) rats, on MXT-mammary carcinomas in $BD2F_1$-mice and on hormone-dependent prostate carcinomas (Dunning R 3327H).

For example, a dose of 5 mg/kg bodyweight against DMBA-induced mammary carcinomas in Sprague-Dawley rats produces complete remission in 74% of the tumors.

The lowest effective dose in the animal test mentioned above is, for example, 2 mg/kg oral 1 mg/kg intravenous 1 mg/kg subcutaneous General dosage ranges for the effect (animal test as described above) are, for example, 5-15 mg/kg oral 3-6 mg/kg intravenous 3-6 mg/kg subcutaneous.

The effect of the compounds according to the invention is comparable with the effect of the known medicament Tamoxifen.

Indications for which the compounds according to the invention may be considered: mammary carcinoma and all oestrogen-dependent tumors (for example endometrium carcinoma), prostate carcinoma, benign prostate hyperplasia.

The pharmaceutical preparations generally contain from 25 to 100 mg and preferably from 40 to 60 mg of the active component(s) according to the invention.

The active component(s) according to the invention may be administered, for example, in the form of tablets, capsules, pills, dragees, suppositories, ointments, jellies, creams, powders, dusting powders, aerosols or in liquid form. Examples of suitable liquid formulations are oily or alcoholic or aqueous solutions and also suspensions and emulsions.

The production of the medicine can be carried out using the known and customary pharmaceutical carriers and diluents as well as other customary assistants. These types of carriers and assistants are set forth, for example, in Ullmann's Encyklopädie der technischen Chemie, Volume 4 (1953), pages 1-39; Journal of Pharmaceutical Sciences 52 (1963), pages 918 et seq.; H. v. Czetsch-Lindenwald, Hilfsstoffe fur Pharmazie und angrenzende Gebiete; Phar. Ind. 2 (1961), pages 72 et seq.; Dr. H. P. Fiedler, Lexicon angrenzende Gebiete, Cantor Kg. Aulendorf in Wurttemberg (1971).

Preferred formulations are tablets containing from 40 to 60 mg active substance or solutions containing from 5 to 10% active substance.

The individual dose of the active components according to the invention may be, for example:

(a) from 40 to 60 mg, preferably 50 mg, in the case of oral formulations (b) from 20 to 30 mg, preferably 25 mg, in the case of parenteral formulations (for example intravenous, intramuscular)

(c) from 5 to 10%, preferably 7.5%, in the case of formulations for local application to the skin and mucous membranes (for example in the form of solutions, lotions, emulsions, ointments, etc.)

(All the doses are based on the free base).

For example, from 1 to 2 tablets containing from 40 to 60 mg active substance may be prescribed three times daily or, for example in the case of intravenous injection, one 10 to 30 ml ampoule containing from 20 to 30 mg substance may be prescribed one to three times daily. With oral administration, the minimum daily dose is for example 50 mg while the maximum daily dose should not exceed 400 mg.

In the case of oral application for example, the acute toxicity of the compounds according to the invention in mice (as expressed by the $LD_{50}$ in mg/kg; Miller and Tainter's method: Proc. Soc. Exper. Biol. a. Med. 57 (1944) 261 is above 2000 mg/kg).

The compounds according to the invention are preferably administered orally and intravenously or even intramuscularly or subcutaneously.

The compositions can comprise, consist essentially of, or consist of the stated materials and the processes can comprise, consist essentially of, or consist of the recited steps with such materials.

DETAILED DESCRIPTION

EXAMPLE 1

2,3-bis-(2-fluoro-4-hydroxyphenyl)-2,3-dimethylbutane

A solution of 3.34 g (0.01 mole) 2,3-bis-(2-fluoro-4-methoxyphenyl)-2,3-dimethylbutane in 250 ml dry methylene dichloride is cooled to $-60°$ C. 7.52 g (0.03 mole) boron tribromide are then added to this solution with stirring in a nitrogen atmosphere. After 30 minutes, the freezing mixture is removed and the reaction mixture is kept at room temperature for 4 hours. 50 cm$^3$ methanol are then added, the reaction mixture is shaken with 2N NaOH and the aqueous phase is extracted with diethylether after neutralization with 3N HCl. The residue obtained after removal of the ether is repeatedly recrystallized from benzene.

MP 168°-169° C. (yield: 88%).

Preparation of the starting material:

17.75 g (0.125 mole) methyliodide are dissolved in diethylether and the resulting solution is added dropwise with stirring to 3.04 g magnesium chips in 15 ml anhydrous ether. The mixture is then heated under reflux for 30 minutes, followed by the dropwise addition with stirring of a solution of 16.82 g (0.1 mole) 2-fluoro-4-methoxy-acetophenone in diethylether. After heating under reflux for 2 hours, the reaction mixture is cooled, poured onto ice and the corresponding deposit dissolved by addition of aqueous NH$_4$Cl solution. The ether phase is separated off, the aqueous phase is extracted with ether, the combined ether phases are washed with aqueous solutions of NaHSO$_3$, NaHCO$_3$ and then with pure water, dried over Na$_2$SO$_4$ and the ether removed. Distillation of the residual oil in a high vacuum gives 14.9 g 2-(2-fluoro-4-methoxyphenyl)-2-propanol.

4.63 g (0.03 mole) titanium trichloride are suspended under nitrogen in 150 cm$^3$ anhydrous dimethoxyethane (glyme) and 0.38 g (0.01 mole) LiAlH$_4$ rapidly added to the resulting suspension while cooling with ice. The dark suspension thus obtained is stirred for 10 minutes. 1.84 g (0.01 mole) 2-(2-fluoro-4-methoxyphenyl)-2-propanol dissolved in 10 cm$^3$ anhydrous dimethoxyethane are then added dropwise with stirring and the mixture heated under reflux for 16 hours. After cooling, the reaction product is decomposed with 2N HCl, diluted with water and extracted with ether. The ether extracts are washed (NaHCO$_3$, H$_2$O) and dried over MgSO$_4$. After removal of the ether, the 2,3-bis-(2-fluoro-4-methoxyphenyl)-2,3-dimethylbutane obtained is recrystallized from toluene/ligroin.

Example 2

2,3-bis-(2-fluoro-4-acetoxyphenyl)-2,3-dimethylbutane

Acetic acid anhydride (306 mg; 3 mmoles) is added dropwise with stirring to an ice-cooled solution of 2,3-bis-(2-fluoro-4-hydroxyphenyl)-2,3-dimethylbutane (306 mg; 1 mmole) in 30 ml pyridine. The reaction mixture is heated for 3 hours to boiling point and hydrolyzed after cooling with ice/H$_2$O. After extraction with CH$_2$Cl$_2$, the combined organic extracts are successively washed repeatedly with 1N HCl, saturated NaHCO$_3$ solution and H$_2$O and dried over MgSO$_4$. After removal of the solvent in vacuo, the product is recrystallized from ethanol.

Colorless crystals; Mp. 160°-161° C. (yield: 84%).

Example 3

2,3-bis-(2-fluoro-4-dichloroacetoxyphenyl)-2,3-dimethylbutane 15 ml dry pyridine are added dropwise with stirring and cooling to a mixture of 2,3-bis-(2-fluoro-4-hydroxyphenyl)-2,3-dimethylbutane (1.53 g; 5 mmoles) and dichloroacetanhydride (6.0 g, 25 mmoles). After the reaction mixture has been stirred for 30 minutes at room temperature, approximately 150 ml 50% aqueous ethanol are added. The deposit is filtered off under suction and washed repeatedly with cold 50% aqueous ethanol. The product is then carefully recrystallized from ethanol by avoiding excessive heating.

Colorless crystals; Mp. 125.5°-126.5° C. (yield: 40%).

Example 4

2,3-bis-(2-fluoro-4-carbamoyloxyphenyl)-2,3-dimethylbutane

Cyanogen bromide (1.27 g; 12 mmoles) is added while cooling with ice to a solution of 2,3-bis-(2-fluoro-4-hydroxyphenyl)-2,3-dimethylbutane (1.53 g; 5 mmoles) in 40 ml absolute acetone. Triethylamine (1.21 g; 12 mmoles) is added dropwise with vigorous stirring; the temperature should not exceed 10° C. during the addition. After stirring for 10 minutes at room temperature, the triethylamine hydrobromide precipitated is filtered off under suction and washed three times with 20 ml acetone. After removal of the solvent is vacuo, the intermediate product obtained (cyanate) is recrystallized from acetone. 30 ml semiconcentrated HCl and 2 ml concentrated H$_2$SO$_4$ are added to the cyanate for hydrolysis and the mixture is heated for 30 minutes to 1 hour until a pale pink coloration of the solution appears. After rapid cooling, the crude product is filtered off under suction and washed liberally with water. The carbamate is recrystallized from ethanol/H$_2$O.

Colorless crystals; Mp. 185.5°-187° C. (yield: 85%, based on the starting phenol).

Example 5

2,3-bis-(2-fluoro-4-phosphatophenyl)-2,3-dimethylbutane

A mixture of 2,3-bis-(2-fluoro-4-hydroxyphenyl)-2,3-dimethylbutane (3.06 g; 0.01 mole), POCl$_3$ (7.75 g; 0.05 mole), 2 ml pyridine and 0.1 ml H$_2$O is heated for 5 hours to boiling temperature. Excess POCl$_3$ is completely removed in vacuo. 20 ml H$_2$O and 15 g of ice are then added and the phosphorylation mixture is stirred in hot. After stirring for 1.5 hours, the deposit is left overnight to settle and the crude product is filtered off under suction. The still moist product is suspended in approximately 15 ml H₂O and stirred for 1 hour at 20° C. After heating to 70° C., the product is filtered off hot under suction. The suspension of the product in 5 ml H₂O is adjusted to pH 7.8 with 4N NaOH, the temperature being at most 40° C. The solution obtained is filtered and 15 ml of a 5N HCl heated to 80° C. are added over a period of 5 minutes. The crude product thus obtained is filtered off hot and dried in vacuo at 50° C. After the compound has been dissolved in and reprecipitated from methanol/ether, it is recrystallized from H₂O.

Colorless crystals; Mp. 191°–193° C. (yield: 42%).

EXAMPLES OF PHARMACEUTICAL PREPARATIONS

Example for Capsules 10 g 2,3-bis-(2-fluoro-4-hydroxyphenyl)-2,3-dimethylbutane (micronized), 106.7 g calcium hydrogen phosphate (Ph.Eur.III) are passed through a 1 mm mesh sieve and mixed. The resulting mixture is moistened with a solution of 2.3 g gelatin (DAB 8) and 1.0 g polysorbate (80 Ph.Eur.III) in 20.7 g water, granulated through a 2 mm mesh sieve and dried at 40° C.

The granulate thus obtained is passed with 20 g cornstarch (Ph.Eur.III) through a 0.8 mm mesh sieve and homogenized. In a suitable capsule machine, this mass is packed in portions of 140 mg in size 3 hard-gelatin insertion capsules. 1 capsule contains 10 mg active principle.

Example for Tablets 10 g 2,3-bis-(2-fluoro-4-carbamoyloxyphenyl)-2,3-dimethylbutane (micronized) and 1-7.6 g calcium hydrogen phosphate (Ph.Eur.III) are mixed and moistened with a solution of 2.3 g gelatin (DAB 8) and 0.1 g polysorbate (80 Ph.Eur.III) in 20.6 g water. The resulting mass is granulated through a 2 mm mesh sieve and dried at 40° C. The granulate thus obtained, 35 g cornstarch (Ph.Eur.III) and 5 g talcum (Ph.Eur.III) are passed through a 0.8 mm mesh sieve and homogenized. The material thus obtained is compressed in a suitable machine to form 7 mm diameter tablets weighing 160 mg. One tablet contains 10 mg active principle.

DAB 8: Deutsches Arzneibuch (German Pharmacopoeia) 8th edition

Ph.Eur.: European Pharmacopoeia, Volume I, II, or III.

Example for an Injection Solution 18 g sodium chloride for parenteral application (Ph.Eur.I) and 5 g 2,3-bis-(2-fluoro-4-phosphatophenyl)-2,3-dimethylbutane are dissolved under nitrogen in 1.8 liters water for injection purposes and made up to 2 liters with water for injection purposes. Under aseptic conditions, the solution is sterile-filtered through a 0.2 μm pore diameter membrane filter. Finally, sterile 2 ml ampoules are filled under nitrogen with 2.15 ml portions of the solution under aseptic conditions. One ampoule contains 5 mg active principle.

The medication can be used in human medicine or in veterinary medicine alone or in a mixture with other pharmacologically active substances.

The entire disclosure of German priority application No. P 3520622.5 is hereby incorporated by reference.

What is claimed is:

1. A compound corresponding to the following formula:

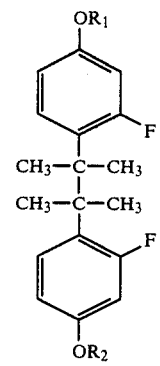

in which the substituents $R_1$ and $R_2$ are hydrogen, an aminocarbonyl group, a $C_1$–$C_6$ alkylaminocarbonyl group, a di-$C_1$–$C_6$-alkylaminocarbonyl group, the group $PO(OH)_2$, a $C_2$–$C_8$ alkanoyl group, a $C_2$–$C_8$ halogen alkanoyl group or a $C_3$–$C_8$ alkenoyl group.

2. A compound according to claim 1 wherein neither $R_1$ nor $R_2$ is hydrogen.

3. A compound according to claim 1 where both $R_1$ and $R_2$ are the group $PO(OH)_2$.

4. A compound according to claim 1 where both $R_1$ and $R_2$ are hydrogen atoms.

5. A compound according to claim 1 where both $R_1$ and $R_2$ are $C_2$–$C_8$ alkanoyl groups.

6. A compound according to claim 1 where $R_1$ and $R_2$ are both $C_2$–$C_8$ halogen alkanoyl groups.

7. A compound according to claim 1 where both $R_1$ and $R_2$ are $C_1$–$C_6$ aminocarbonyl groups.

8. A compound according to claim 1 where $R_1$ and $R_2$ are selected from the group consisting of hydrogen, $C_2$–$C_8$ alkanoyl and $C_2$–$C_8$ halogen alkanoyl.

9. A process for producing a compound corresponding to the following formula:

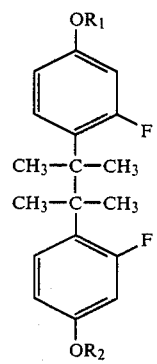

in which the substituents $R_1$ and $R_2$ represent hydrogen, an aminocarbonyl group, a $C_1$–$C_6$ alkylaminocarbonyl group, a di-$C_1$–$C_6$-alkylaminocarbonyl group, the group $PO(OH)_2$, a $C_2$–$C_8$ alkanoyl group, a $C_2$–$C_8$ halogen alkanoyl group or a $C_3$–$C_8$ alkenoyl group, comprising in a compound corresponding to the following formula:

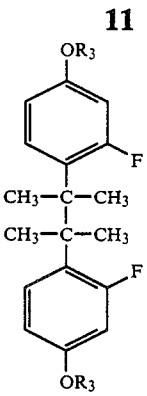

in which $R_3$ is a $C_1$–$C_4$ alkyl group eliminating these two alkyl groups and optionally acylating the resulting compound formula I, in which the two substituents $R_1$ and $R_2$ are hydrogen by the substituents $R_1$ and $R_2$ having other than hydrogen, and optionally converting $C_3$–$C_8$ halogen alkanoyl groups present in the resulting compounds into $C_3$–$C_8$ alkenoyl groups by elimination of hydrogen halide.

10. A pharmaceutical composition containing a compound according to claim 1 and a carrier, diluent or adjuvant.

* * * * *